(12) United States Patent
Beattie

(10) Patent No.: US 12,642,902 B2
(45) Date of Patent: Jun. 2, 2026

(54) INFUSING DISSOLVED OXYGEN INTO I.V. FLUIDS TO PROVIDE SHORT TERM EMERGENCY OXYGENATION OF VENOUS BLOOD FOR COMPROMISED OR TRAUMA PATIENTS

(71) Applicant: GIS Ventures Inc., Saint Andrews (CA)

(72) Inventor: Michael Beattie, Saint Andrews (CA)

(73) Assignee: GIS Ventures Inc., Saint Andrews (CA)

( * ) Notice: Subject to any disclaimer, the term of this patent is extended or adjusted under 35 U.S.C. 154(b) by 775 days.

(21) Appl. No.: 17/995,723

(22) PCT Filed: Apr. 7, 2021

(86) PCT No.: PCT/CA2021/050463
§ 371 (c)(1),
(2) Date: Oct. 7, 2022

(87) PCT Pub. No.: WO2021/203199
PCT Pub. Date: Oct. 14, 2021

(65) Prior Publication Data
US 2023/0166018 A1    Jun. 1, 2023

Related U.S. Application Data

(60) Provisional application No. 63/006,339, filed on Apr. 7, 2020.

(51) Int. Cl.
*A61M 1/32* (2006.01)

(52) U.S. Cl.
CPC ....... *A61M 1/32* (2013.01); *A61M 2202/0208* (2013.01); *A61M 2202/0266* (2013.01); *A61M 2205/50* (2013.01)

(58) Field of Classification Search
CPC ............ A61M 1/32; A61M 2202/0208; A61M 2202/0266; A61M 2205/50;
(Continued)

(56) References Cited

U.S. PATENT DOCUMENTS

2004/0079359 A1*    4/2004    Aylsworth ............ A61M 16/10
                                                   128/200.14
2013/0230602 A1      9/2013    Grady et al.
(Continued)

FOREIGN PATENT DOCUMENTS

JP          7-136251            5/1995
JP          2003-532448 A       4/2001
(Continued)

OTHER PUBLICATIONS

Japanese Office Action received from JPO mailed Jul. 8, 2025 for related JP Patent Application No. 2022-561138 derived from PCT/CA2021/050463 in the name of GIS Ventures Inc.
(Continued)

*Primary Examiner* — Susan S Su
*Assistant Examiner* — Erin A Kim
(74) *Attorney, Agent, or Firm* — Crowe & Dunlevy, P.C.

(57)    ABSTRACT

This invention relates to a process through which intravenous fluids, blood, or artificial blood containing high-levels of mechanically-injected dissolved oxygen can be used to maintain appropriate oxygen levels in the venous blood and thereby provide short-term oxygenation support for compromised or trauma patients. In one aspect, there is provided a system and process for oxygenating a biological fluid for use in a compromised or a trauma subject in need of oxygenation support to maintain appropriate oxygen levels in the subject, the process comprising: supplying oxygen gas
(Continued)

from an oxygen source; and dissolving an amount of the supplied oxygen into a biological fluid to obtain an oxygen enriched biological fluid.

10 Claims, 3 Drawing Sheets

(58) Field of Classification Search
CPC .. A61M 2202/0007; A61M 2202/0476; A61M 2230/435; B01F 23/23; B01F 23/237612; A61B 5/145
See application file for complete search history.

(56) References Cited

U.S. PATENT DOCUMENTS

| 2017/0281063 A1 | 10/2017 | Utsugida et al. |
| 2018/0311071 A1 | 11/2018 | Burnett et al. |

FOREIGN PATENT DOCUMENTS

| JP | 2012-228284 A | 11/2012 | |
| JP | 2013-532538 A | 8/2013 | |
| WO | WO-0126709 A2 * | 4/2001 | .......... A61M 1/1698 |
| WO | 2014118653 A1 | 8/2014 | |
| WO | 2018185464 A1 | 10/2018 | |

OTHER PUBLICATIONS

Japanese Office Action received from JPO mailed Nov. 14, 2024 for related JP Patent Application No. 2022-561138 derived from PCT/CA2021/050463 in the name of GIS Ventures Inc.
"PCT/CA2021/050463 International Preliminary Report on Patentability and Written Opinion of the International Searching Authority" dated Oct. 6, 2022.
Extended European Search Report; application No. 21784596.5 dated Apr. 10, 2024.
"Written Opinion of the International Search Authority in PCT/CA2021/050463 dated Jul. 2, 2021".
"International Search Report in PCT/CA2021/050463 dated Jul. 2, 2021".

* cited by examiner

INFUSING DISSOLVED OXYGEN INTO I.V. FLUIDS TO PROVIDE SHORT TERM EMERGENCY OXYGENATION OF VENOUS BLOOD FOR COMPROMISED OR TRAUMA PATIENTS

CROSS REFERENCE TO RELATED APPLICATIONS

The present application claims priority from U.S. provisional patent application No. 63/006,339, entitled "INFUSING DISSOLVED OXYGEN INTO I.V. FLUIDS TO PROVIDE SHORT TERM EMERGENCY OXYGENATION OF VENOUS BLOOD FOR COMPROMISED OR TRAUMA PATIENTS", filed Apr. 7, 2020, which is incorporated herein by reference.

FIELD

The present disclosure relates to a system and a process of infusing oxygen into intravenous fluids, blood, or artificial blood to provide short-term oxygenation support for compromised or trauma patients. In aspects, the process produces intravenous fluids, blood, or artificial blood containing high-levels of mechanically-injected dissolved oxygen to maintain appropriate oxygen levels in the venous blood when delivered to the compromised or trauma patients.

BACKGROUND

A long-standing medical problem concerns the oxygenation of venous blood for compromised or trauma patients. Patients can have compromised lung function due to disease which impairs lung function such as pneumonia or a viral infection or Chronic Obstructive Pulmonary Disease, or due to induced trauma such as through a gun-shot or automotive accident, or due to surgical procedure such as during a lung transplant.

The present approaches for providing oxygen to patients comprise the following:

Mask or nasal tubes with variable percentages of pure oxygen (80-100%)

Intubation and connection to a mechanical respirator/ventilator

External Corporeal Membrane Oxygenation (ECMO), removing blood from the patient and passing it by a membrane which allows oxygen to transfer to the hemoglobin in the blood and then shunting the oxygenated blood back into the patient With respect to these approaches, masks only work if the lungs are not severely compromised and sufficient gas exchange is still occurring in the lungs. As such, masks are not sufficient for cases involving chest wounds, high fluid levels in the lungs, or compromised diaphragm muscle/nerve stimulation.

Regarding intubation, this is a high-risk procedure that causes lung trauma of and on its own. As a result of this trauma, there is a serious risk that patients will either die or be unable to be removed from these machines.

Finally, note that ECMO machines are extremely expensive and non-portable equipment for use in a sterile environment such as a surgical suite and entail significant time delays due to procedures for implementation. At the same time, ECMO machines present the promise that lung function can be temporarily, but sufficiently, replaced by ensuring that appropriate levels of oxygen are maintained in the blood.

Accordingly, there is a need for improved systems for oxygenation of blood of compromised and/or trauma patients and improved processes for infusing oxygen into intravenous fluids, blood, or artificial blood to provide short-term oxygenation support for compromised or trauma patients.

SUMMARY OF THE INVENTION

The present disclosure relates to a system and a process of infusing oxygen into intravenous fluids, blood, or artificial blood to provide short-term oxygenation support for compromised or trauma patients.

In aspects, the process produces intravenous fluids, blood, or artificial blood containing high-levels of mechanically-injected dissolved oxygen to maintain appropriate oxygen levels in the venous blood when delivered to the compromised or trauma patients.

In one embodiment, the present disclosure relates to a process for oxygenating a biological fluid for use in a compromised or a trauma subject in need of oxygenation support to maintain appropriate oxygen levels in the subject, the process comprising:

supplying oxygen gas from an oxygen source; and dissolving an amount of the supplied oxygen into a biological fluid to obtain an oxygen enriched biological fluid.

In one aspect, the process further comprises a step of removing an amount of a first gas that is substantially equivalent the amount of the supplied oxygen dissolved into the biological fluid.

In one aspect, the steps of dissolving the amount of the supplied oxygen and removing the amount of the first gas are carried out simultaneously to avoid any increase in total gas pressure (TGP) so as to at least reduce or prevent the formation of gas emboli in the bloodstream of the subject when the oxygen enriched biological fluid is introduced into the subject.

In one aspect, the first gas is nitrogen.

In one aspect, the process further comprises a step of directing the oxygen enriched biological fluid into a compatible reservoir or a step of delivering the oxygen enriched biological fluid directly into the circulation of the subject.

In one aspect, the compatible reservoir is an IV bag or a bottle.

In one aspect, the step of delivering comprises injecting the oxygen enriched biological fluid directly into the venous circulation of the subject.

In one aspect, the oxygen enriched biological fluid has a high level of dissolved oxygen.

In one aspect, the oxygen enriched biological fluid has greater than at about 100% oxygen saturation.

In one aspect, the oxygen enriched biological fluid has at least around 400% oxygen saturation.

In one aspect, the biological fluid is sterile water, intravenous (IV) fluid, blood, or artificial blood.

In one aspect, the artificial blood is hemoglobin-based oxygen carriers (HBOC's) or perflourocarbons (PFC's).

In a further aspect, the HOBC is oxyglobin.

In one aspect, the subject is a human or a non-human animal.

In one embodiment, the present disclosure relates to an oxygen enriched biological fluid produced according to a process, the process comprising:

supplying oxygen gas from an oxygen source; and dissolving an amount of the supplied oxygen into a biological fluid to obtain an oxygen enriched biological fluid.

In one embodiment, the present disclosure relates to use of the oxygen enriched biological fluid in a compromised or a trauma subject in need of oxygenation support to maintain appropriate oxygen levels in the subject.

In one embodiment, the present disclosure relates to a method of oxygenating blood of compromised and/or trauma patients comprising administering the oxygen enriched biological fluid to a compromised or a trauma subject in need of oxygenation support to maintain appropriate oxygen levels in the subject.

In one embodiment, the present disclosure relates to a system for administering an oxygen enriched biological fluid to a compromised or a trauma subject in need of oxygenation support to maintain appropriate oxygen levels in the subject, the system comprising:

an oxygen sensor probe configured to obtain arterial oxygen saturation of a subject and to output one or more signals dependent on the obtained level of arterial oxygen saturation;

a processor;

at least one memory device including instructions embodied thereon, wherein the instructions, when executed by the processor, cause the processor to identify one or more signals indicative of a level of arterial oxygen saturation below a threshold range of appropriate oxygen saturation levels;

a source of oxygen enriched biological fluid; and a regulator controlled by the processor and configured to deliver an amount of the oxygen enriched biological fluid to the subject when the processor identifies one or more signals indicative of a level of arterial oxygen saturation below the threshold range of appropriate oxygen saturation levels.

In one embodiment, the present disclosure relates to a method of administering an oxygen enriched biological fluid to a compromised or a trauma subject in need of oxygenation support to maintain appropriate oxygen levels in the subject, the method comprising:

sensing the level of arterial oxygen saturation of a subject using an oxygen sensor probe; and controlling a regulator increase the rate of delivery of an oxygen enriched biological fluid if the sensed level is below a threshold range of appropriate oxygen levels.

In one aspect, the regulator comprises an IV drip machine.

BRIEF DESCRIPTION OF THE DRAWINGS

Reference will now be made, by way of example, to the accompanying drawings which show example embodiments of the present application, and in which.

DETAILED DESCRIPTION OF THE EXAMPLE EMBODIMENTS

With reference to FIGS. 1 to 4, there is provided a first general embodiment, which relates to system and a process through which intravenous fluids containing high-levels of mechanically-injected dissolved oxygen can be used to maintain appropriate oxygen levels in venous blood and thereby provide short-term oxygenation support for compromised or trauma patients.

Pre-packaged commercial Intravenous (IV) fluids are generally comprised of the following Sterile water Salts, sugars or colloids May contain alkalinizing agents to control respiratory acidosis May combine with added drug infusion Types of IV fluids, or drips, which are generally administered into the patient's vein(s), including the following:

Lactated ringer's solutions with and without salts or sugars

Isotonic solutions 0.9% NaCL, lactate, 5% Dextrose

Hypotonic solutions 0.45% NaCl, 0.5% NaCl, 0.33% NaCl

Hypertonic solutions

5% Dextrose, 10% Dextrose, 3% NaCl, 25% Albumin, TPN solutions

Colloid solutions

Plasmagel, Polygeline, Dextron, Hespan, Plasmanate

While there are a variety of compositions for IV-fluid bags, they are all assembled in a sterile environment from a pool of sterilized water.

Figure 1:
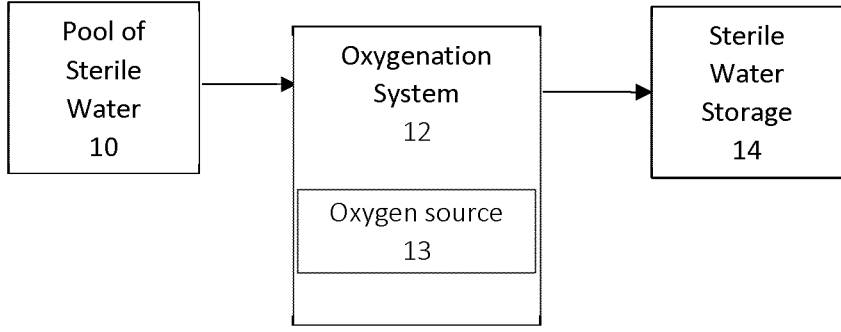
FIG. 1 shows a schematic of sterile water oxygenation process.

In one embodiment, the present invention comprises a two-stage process:

As shown in FIG. 1, a sterile water supply 10 is contacted with an oxygenation system 12 comprising a source of oxygen 13. High-levels of dissolved oxygen are infused into the sterile water supply 10 to produce an enriched sterile water supply 14, prior to packaging the commercial IV bags/bottles 16 for use with any known IV drip regulators 18 as shown in FIG. 3.

Figure 3:
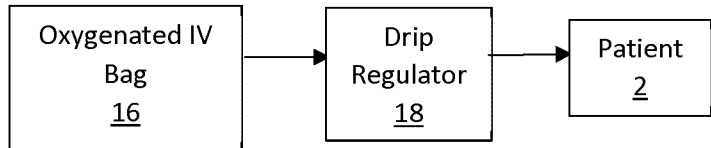
FIG. 3 shows a schematic of a process for injection of oxygenated intravenous fluid.

As shown in FIG. 3, the IV drip 18 then provides the needed dissolved oxygen to the hemoglobin in the venous system of a subject 2. In some aspects, the hemoglobin can be that found in natural or artificial blood.

Figure 4:
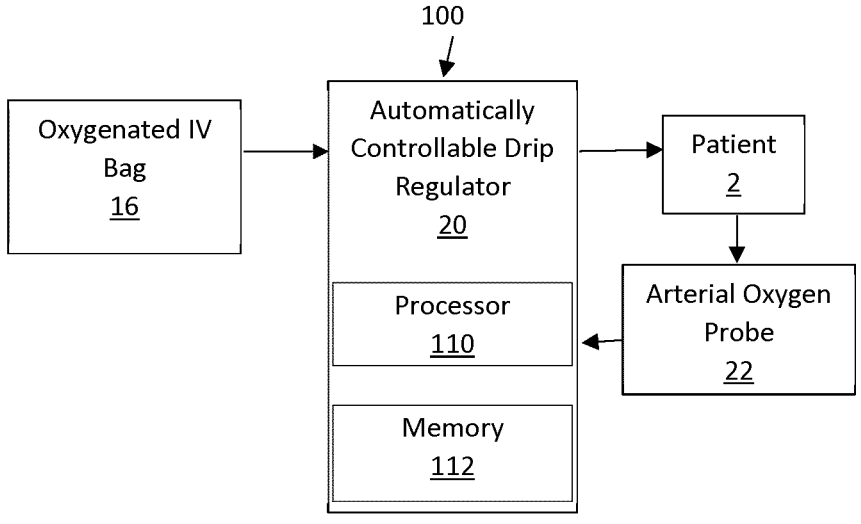
FIG. 4 shows a schematic of a process for controlled injection of oxygenated intravenous fluid.

As shown in FIG. 4, the process can be further enhanced by using an automated feedback control system 100 comprising a processor 110 and at least one memory device 112 where the measurements and resulting signals from one or more arterial oxygen probes 22 cause the system 100 to actuate a regulator 20 of the IV-drip machine 18 to mechanically control and regulate the drip rate of the source of oxygen enriched biological fluid 16 and thus the arterial dissolved-oxygen levels in a patient.

In particular, the oxygen sensor probe 22 is configured to obtain arterial oxygen saturation of the patient/subject 2 and to output one or more signals dependent on the obtained level of arterial oxygen saturation. The at least one memory device 110 including instructions embodied thereon, wherein the instructions, when executed by the processor 110, cause the processor 110 to identify one or more signals indicative of a level of arterial oxygen saturation below a threshold range of appropriate oxygen saturation levels. A source of oxygen enriched biological fluid 16 is provided to the system 100 and the regulator 20 which is controlled by the processor 110 is configured to deliver an amount of the oxygen enriched biological fluid 16 to the patient/subject 2 when the processor 100 identifies one or more signals indicative of a level of arterial oxygen saturation below the threshold range of appropriate oxygen saturation levels.

In aspects, the threshold range of appropriate oxygen saturation levels is less than about 100%, less than about 95%, less than about 90%, or less than about 85%.

One advantage of this invention is that the resulting oxygen-infused IV bags/bottles 16 are inherently portable which enables wide use in the field. These bags 16 can be used in hospital rooms, hospital emergency rooms and surgical suites, ambulances, epidemics and pandemics, armed conflicts, World Health Organization and state declared emergencies, etc.

The are some techniques for infusing high dissolved oxygen levels into an aquatic environment. For those who are skilled in the art, the injection of oxygen into water can be done in a variety of ways. For example, this can be done through micro-bubble diffusion, molecular-level infusion, membrane osmosis, etc.

A key issue in the oxygenation of IV fluids is to avoid increasing the dissolved gas pressure to the point that IV injection into the blood stream causes emboli to be formed in the blood (i.e. The Bends or Gas Bubble Disease) which can be lethal. Note that this most commonly occurs from nitrogen being released from the blood stream as the victim moves from a high-pressure environment to a low-pressure environment.

In one aspect, the system and process provides for high levels of dissolved oxygen in the IV fluids. In some aspects, the system and process provides for IV fluids having greater than at about 100% oxygen saturation. In further aspects, the dissolved oxygen in IV fluids can be increased to 400% of saturation and above without causing emboli when injected into the blood stream.

Figure 5:
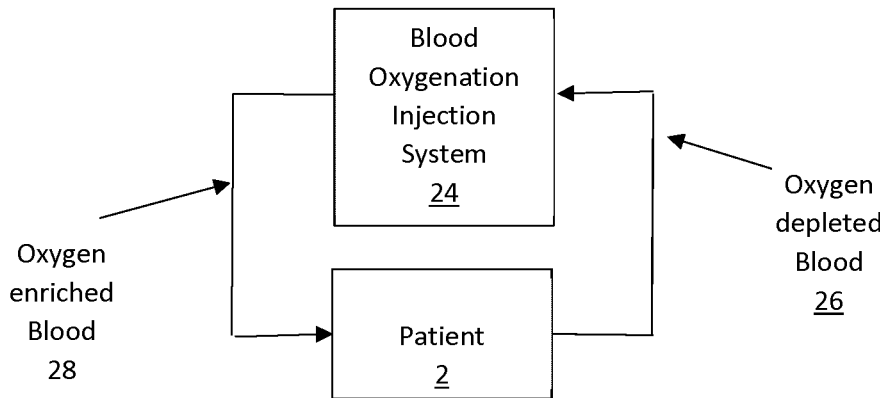
FIG. 5 shows a schematic of a process for infusion of oxygen into blood by flow through processing.
Figure 6:
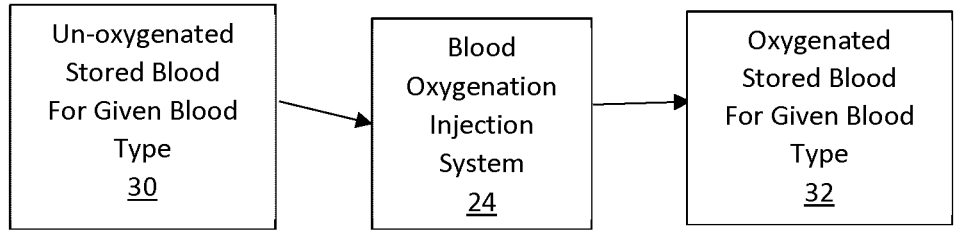
FIG. 6 shows a schematic of a process for infusion of oxygen into blood by batch processing.
Figure 7:
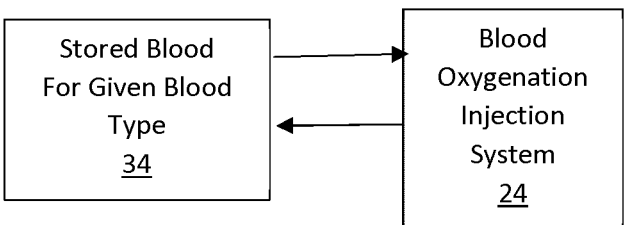
FIG. 7 shows a schematic of process for infusion of oxygen into blood by using recycling.

With reference to FIGS. 5 to 7, there is provided a second general embodiment, which relates to an alternative to ECMO machines for directly infusing oxygen into blood.

As shown in FIG. 5, in this embodiment of the invention, a blood oxygenation system 24 comprising an oxygen source (13) is used to directly infuse oxygen into blood or artificial blood 26 to produce oxygen enriched blood or artificial blood 26. The produced enriched blood or artificial blood 26 can either be used in flow-through as in a surgical suite as shown in FIG. 5. Alternatively, blood oxygenation system 24 can be used to infuse oxygen into blood or artificial blood of a given blood type 30 to produce oxygen enriched blood or artificial blood for a given blood type 32 in batch for storage as shown in FIG. 6.

Whereas, ECMO machines use a membrane process for oxygenation while maintaining the dissolved gas pressure, this embodiment uses existing micro-diffusion or molecular infusion processes while maintaining the dissolved gas pressure to prevent the formation of emboli in blood or artificial blood.

With regard to the direct oxygenation of blood and artificial blood, this includes all classes of hemoglobin-based oxygen carriers (HBOC's), such as Oxyglobin approved by the FDA/Europe for veterinary purposes and all classes of perflourocarbons (PFC's).

Figure 2:
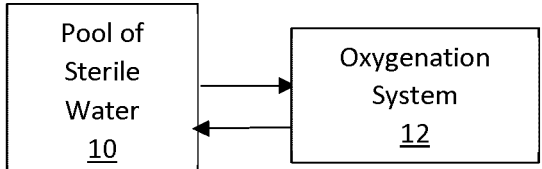
FIG. 2 shows an alternative schematic of sterile water oxygenation process featuring recycling.

According to embodiment as shown in FIG. 2, the pool of sterile water 10 can be treated with the oxygenation system 12 to continually increase and/or replenish the oxygen content of the pool 10. Similarly, as shown in FIG. 7, a pool of blood or artificial blood of a given blood type 34 can be treated with the oxygenation system 24 to continually increase and/or replenish increase the oxygen content of the pool 34.

According to embodiment, the disclosed system and process can find broad use in both humans and non-human animals.

The various embodiments presented above are merely examples and are in no way meant to limit the scope of this disclosure. Variations of the innovations described herein will be apparent to persons of ordinary skill in the art having the benefit of the example embodiments, such variations being within the intended scope of the present disclosure. In particular, features from one or more of the above-described embodiments may be selected to create alternative embodiments comprised of a sub-combination of features, which may not be explicitly described above. In addition, features from one or more of the above-described embodiments may be selected and combined to create alternative embodiments comprised of a combination of features which may not be explicitly described above. Features suitable for such combinations and sub-combinations would be readily apparent to persons skilled in the art upon review of the present disclosure as a whole. The subject matter described herein intends to cover and embrace all suitable changes in technology.

Certain adaptations and modifications of the described embodiments can be made. Therefore, the above discussed embodiments are considered to be illustrative and not restrictive.

The invention claimed is:

1. A process for oxygenating a biological fluid for use in a compromised or a trauma subject in need of oxygenation support to maintain appropriate oxygen levels in the subject, the process comprising:

supplying oxygen gas from an oxygen source;

dissolving an amount of the supplied oxygen into a biological fluid to obtain an oxygen enriched biological fluid;

removing an amount of nitrogen gas that is substantially equivalent to the amount of the supplied oxygen dissolved into the biological fluid, wherein, the steps of dissolving the amount of the suppled oxygen and removing the amount of the nitrogen gas are carried out simultaneously to avoid any increase in total gas pressure (TGP) so as to at least reduce or prevent the formation of gas emboli in the bloodstream of the subject when the oxygen enriched biological fluid is introduced into the subject; and directing the oxygen enriched biological fluid into a compatible reservoir or delivering the oxygen enriched biological fluid directly into the circulation of the subject.

2. The process according to claim 1 wherein the compatible reservoir is an IV bag or a bottle.

3. The process according to claim 1 wherein the step of delivering comprises injecting the oxygen enriched biological fluid directly into the venous circulation of the subject.

4. The process according to claim 3 wherein the oxygen enriched biological fluid has a high level of dissolved oxygen.

5. The process according to claim 4 wherein the oxygen enriched biological fluid has greater than at about 100% oxygen saturation.

6. The process according to claim 5 wherein the oxygen enriched biological fluid has at least around 400% oxygen saturation.

7. The process according to claim 6 wherein the biological fluid is sterile water, intra-venous (IV) fluid, blood, or artificial blood.

8. The process according to claim 7 wherein the artificial blood is hemoglobin-based oxygen carriers (HBOC's) or perflourocarbons (PFC's).

9. The process according to claim 8 wherein the HBOC is oxyglobin.

10. The process according to claim 9, wherein the subject is a human or a non-human animal.

\* \* \* \* \*